United States Patent [19]

Beschke et al.

[11] 4,447,615
[45] May 8, 1984

[54] PROCESS FOR THE PURIFICATION OF NICOTINIC ACID AMIDE I

[75] Inventors: Helmut Beschke, Hanau; Franz-Ludwig Dahm, Alzenau; Heinz Friedrich; Günter Prescher, both of Hanau, all of Fed. Rep. of Germany

[73] Assignee: Degussa Aktiengesellschaft, Frankfurt, Fed. Rep. of Germany

[21] Appl. No.: 288,186

[22] Filed: Jul. 29, 1981

[30] Foreign Application Priority Data

Jul. 30, 1980 [DE] Fed. Rep. of Germany ....... 3028904

[51] Int. Cl.$^3$ .................. C07D 211/72; C07D 211/84; C07D 213/56
[52] U.S. Cl. ..................................... 546/317; 546/316
[58] Field of Search ................................. 546/316, 317

[56] References Cited

U.S. PATENT DOCUMENTS

| 2,412,749 | 12/1946 | Pike | 546/316 |
|---|---|---|---|
| 2,471,518 | 5/1949 | Duesel | 546/316 |
| 3,678,060 | 7/1972 | Finkelstein | 546/316 |
| 4,080,336 | 3/1978 | Said | 546/316 |

FOREIGN PATENT DOCUMENTS

| 87228 | 7/1959 | Denmark | 546/316 |
|---|---|---|---|
| 828247 | 7/1953 | Fed. Rep. of Germany | 546/316 |
| 2517054 | 11/1976 | Fed. Rep. of Germany | 546/316 |
| 879551 | 11/1961 | United Kingdom | 546/316 |

OTHER PUBLICATIONS

Krewson J. Amer. Chem. Soc. vol. 65, pp. 2256–2257 (1943).
Galat J. Amer. Chem. Soc. vol. 70, p. 3945 (1948).

*Primary Examiner*—Henry R. Jiles
*Assistant Examiner*—Robert C. Whittenbaugh
*Attorney, Agent, or Firm*—Cushman, Darby & Cushman

[57] ABSTRACT

Crude nicotinamide is purified by a recrystallization and in this way freed especially from nicotinic acid and salts of nicotinic acid. As solvent there is used a 2-methylpropanol-1 containing water. The recrystallization takes place at a pH between about 7 and 10.

16 Claims, No Drawings

PROCESS FOR THE PURIFICATION OF NICOTINIC ACID AMIDE I

BACKGROUND OF THE INVENTION

The invention is directed to a process for the recovery of pure nicotinamide from crude nicotinamide by recrystallization in alkanol. The invention particularly is directed to a process for freeing the nicotinamide from the impurities nicotinic acid and salts of nicotinic acid, e.g. sodium nicotinate, ammonium nicotinate and potassium nicotinate.

Nicotinamide is generally produced by hydrolysis of nicotinonitrile in acid or alkaline medium or by reaction of nicotinic acid with ammonia. The crude nicotinamide obtained in this process of production contains impurities, especially nicotinic acid (generally about 0.3 to 5.0%) and salts of nicotinic acid (generally about 1.5 to 2.5%). These impurities create problems in the further use of the nicotinamide, namely in the pharmaceutical area, especially if their amount exceeds 0.1%.

It is known to purify crude nicotinamide with the help of an ion exchange resin (British Pat. No. 879551 and Finkelstein U.S. Pat. No. 3,678,060). These processes are expensive and besides only give a sufficiently pure nicotinamide under a considerable loss of yield. It is also known to purify crude nicotinamide by recrystallization. As solvents in this case there are employed acetone (Duesel, U.S. Pat. No. 2,471,518), propanol-2 or butyl acetate in the presence of decolorizing carbon (German Pat. No. 828247), ethyl acetate (Krewson, J. Amer. Chem. Soc., Vol. 65, pages 2256–2257 (1943)), ethanol in the presence of activated carbon (Galat, J. Amer. Chem. Soc., Vol. 70, page 3945 (1948)), dioxane or petroleum ether (Pike U.S. Pat. No. 2,412,749) or benzene (Danish Pat. No. 87228).

A disadvantage of these processes is that for the production of a sufficiently pure nicotamide multiple recrystallization is required and only a moderate yield of pure nicotinamide is produced.

SUMMARY OF THE INVENTION

There has now been found a process for the recovery of pure nicotamide from crude nicotamide by recrystallization in alkanol which is characterized by the recrystallization being carried out in 2-methylpropanol-1 containing water at a pH of about 7 to 10. In this process an outstandingly pure nicotamide is obtained with favorable yield with only a single recrystallization.

The process of the invention is suitable for the purification of crude nicotinamide as it is obtained from the reaction mixture as it is obtained in the customary processes for the production of nicotinamide, especially in the hydrolysis of nicotinonitrile in acid or alkaline medium or in the reaction of nicotinic acid with ammonia. With advantage there is used the process for the purification of the nicotinamide produced by the process of German OS No. 2517054. The entire disclosure of German OS No. 2517054 is hereby incorporated by reference and relied upon.

To carry out the process of the invention the crude nicotinamide is recrystallized from 2-methylpropanol-1 which suitably contains 1 to 18 weight percent of water. It is advantageous to employ 2-methylpropanol-1 containing 10 to 18 weight percent of water. It is particularly preferred to use 2-methylpropanol-1 saturated with water.

The crude nicotinamide for the recrystallization is suitably adjusted to a pH of between about 7 and 10 and with advantage in the solution of nicotinamide in 2-methyl-propanol-1 containing water that has been heated to 80° to 100° C. for recrystallisation. Preferably there is chosen a pH of 7.2 to 9.8, especially from 7.5 to 9.5. The establishment of the pH is made as required by addition of either acid, for example acetic acid, or alkali, for example sodium hydroxide.

The mother liquor remaining after the recrystallization and separation of the pure nicotinamide is advantageously used for further recrystallization. In the continuous form of the process the mother liquor is repeatedly recycled, but in order to avoid an undesired enrichment of the impurities in the mother liquor from time to time or suitably in each cycle, there is removed a portion of the mother liquor according to the degree of impurities. It is advantageous to work up this portion of the mother liquor and for example, to either separate the 2-methylpropanol-1 and the nicotinamide by distillation and return it to the cycle or preferably to remove the impurities by treatment with ion exchangers and to reuse the remaining purified mother liquor. Thus there can be used e.g. a cation exchange resin such as sulfonated styrene-divinyl benzene copolymer or an anion exchange such as a strongly basic styrene-divinyl benzene copolymer quaternary ammonium resin, e.g. Amberlite IRA 400 or Dowex 1. Additional suitable ion exchange resins are shown in Finkelstein U.S. Pat. No. 3,678,060, the entire disclosure of which is hereby incorporated by reference and relied upon.

Unless otherwise indicated all parts and percentages are by weight.

The process can comprise, consist essentially of or consist of the stated steps with the materials set forth.

DETAILED DESCRIPTION

EXAMPLE 1

There were mixed 250 grams of crude nicotinamide which contained 2.3% sodium nicotinate and 0.7% nicotinic acid with 260 ml of 2-methylpropanol-1 and 37 ml of water. The mixture was heated to the boiling point and thereby the nicotinamide dissolved. The solution was cooled to 80° C. The pH of the mixture was 6.6. By dropwise addition of 5.3 ml of 10 percent aqueous sodium hydroxide solution, the pH was raised to 7.9. Subsequently the mixture was slowly cooled to 10° C. The nicotinamide crystallized out was filtered off with suction, washed three times, each time with 50 ml of anhydrous 2-methyl-propanol-1, and dried. The yield was 180 grams, corresponding to 74% based on the nicotinamide in the crude material employed. Nicotinic acid was not detectable in the nicotinamide recovered. The sodium content was 0.001%.

EXAMPLE 2

The procedure was as in Example 1 but the pH was adjusted to 7.3 by the addition of 5.1 ml of the sodium hydroxide solution. The yield was 174 grams, corresponding to 72%. The product had the same purity as the product obtained in Example 1.

EXAMPLE 3

There were present 320 grams of a mother liquor which was obtained in one of the above-mentioned recrystallizations. At the boiling point there was dissolved in this 180 grams of crude nicotinamide which contained 2.3% of sodium nicotinate and 0.7% nicotinic acid. By addition of 3.9 ml of a 10 percent aqueous sodium hydroxide solution the pH was adjusted to 7.9. Then the mixture was cooled to 10° C. The nicotinamide which crystallized out was filtered off with suction, washed three times, each time with 50 ml of anhydrous 2-methylpropanol-1 and dried. The yield was 171 grams, corresponding to 98% based on the nicotinamide present in the crude material employed. The product had the same purity as the product obtained according to Example 1.

EXAMPLE 4

There was used the mother liquor obtained in the recrystallization according to Example 3. There were separated off 195 grams from the total amount of 320 grams, and the portion separated off was distilled at 145° C. and 1 mbar. There were recovered thereby besides the solvent 7 grams of pure nicotinamide. The residual 225 grams of mother liquor after addition of 78 grams of 2-methylpropanol-1 and 6 grams of water was used for a further recrystallization. For this purpose there were employed 109 grams of crude nicotinamide which contained 2.3% of sodium nicotinamide and 0.7% of nicotinic acid. Otherwise the process was as in Example 3. The yield was 97 grams, corresponding to 91% based on the nicotinamide in the crude material employed. The product had the same purity as the product obtained in Example 1. The mother liquor in each case after separation of a 95 gram portion and addition of 78 grams of 2-methylpropanol-1 and 6 grams of water was used for additional like recrystallizations.

EXAMPLE 5

The procedure was as in Example 3 but there were used 10 times the amounts. There accumulated 3300 grams of mother liquor in the recrystallization. There was separated off from this and purified a portion of 1100 grams. For this purpose, the liquid portion was first passed over a column of a strongly acid cation exchanger (sulfonated styrene-divinyl benzene copolymer). The throughput velocity was 3.5 liters of liquid per liter of exchanger per hour. The exchanger was used up to a capacity of 1.62 val per liter of exchanger and resulted in a lowering of the content of sodium ions in the liquid to below 1 ppm based on the content of nicotinamide in the liquid. The liquid was then led over an anion exchanger (e.g. Amberlite IRA-400). This was used up to a capacity of 0.38 val per liter of exchanger and caused the content of nicotinate ions to be reduced to below 0.02% based on the content of nicotinamide in the liquid. The thus purified portion of the mother liquor was combined with the remaining mother liquor and used for a further recrystallization. Hereby the procedure was as in Example 3 but the materials were employed in 10 times the amount. The product had the same purity as the product obtained in Example 1. The yield was 93%. The cation exchanger was regenerated by treatment with dilute aqueous hydrochloric acid and the anion exchanger was regenerated by treatment with dilute aqueous sodium hydroxide solution. Thereby there were obtained 47 grams of sodium nicotinate.

The entire disclosure of German priority application No. P 3028904.4 is hereby incorporated by reference.

What is claimed is:

1. In a process for the recovery of pure nicotinamide from a crude nicotinamide by recrystallization in an alcohol, the improvement comprising carrying out the recrystallization in 2-methyl-propanol-1 containing water at a pH between 7 and 10 and including the steps of at least once recycling the mother liquor from the recrystallization of the crude nicotinamide, heating the mother liquor, adding further crude nicotinamide to the heated mother liquor, cooling the mother liquor containing said further crude nicotinamide sufficiently to recrystallize the crude nicotinamide in purer form.

2. The process of claim 1 wherein the 2-methyl-propanol-1 is saturated with water.

3. The process of claim 1 wherein the 2-methyl-propanol-1 contains 1 to 18% water.

4. The process of claim 3 wherein the 2-methyl-propanol-1 contains 10 to 18% water.

5. The process of claim 3 wherein the crude nicotinamide contains (1) 0.3 to 5.0% of nicotinic acid or (2) 1.5 to 2.5% of a salt of nicotinic acid or a mixture of (1) and (2) and the content of nicotinic acid and the salt of nicotinic acid is reduced to an amount of not over 0.1% in a single recrystallization.

6. The process of claim 5 wherein the 2-methyl-propanol-1 contains 10 to 18% water.

7. The process of claim 6 wherein the crude nicotinamide contains nicotinic acid and sodium nicotinate.

8. The process of claim 5 wherein the salt is the sodium salt or the ammonium salt.

9. A process according to claim 1 including the steps in at least one of the recyclings removing a portion of the mother liquor from the cycle, removing impurities from 2-methylpropanol-1 said portion of the mother liquor, and returning the thus purified portion of the mother liquor to the cycle.

10. A process according to claim 2 including the steps in at least one of the recyclings removing a portion of the mother liquor from the cycle, removing impurities from 2-methylpropanol-1 said portion of the mother liquor, and returning the thus purified portion of the mother liquor to the cycle.

11. A process according to claim 3 including the steps in at least one of the recyclings removing a portion of the mother liquor from the cycle, removing impurities from 2-methylpropanol-1 said portion of the mother liquor, and returning the thus purified portion of the mother liquor to the cycle.

12. A process according to claim 9 including the steps in at least one of the recyclings removing a portion of the mother liquor from the cycle, removing impurities from 2-methylpropanol-1 said portion of the mother liquor, and returning the thus purified portion of the mother liquor to the cycle.

13. A process according to claim 1 wherein all of the mother liquor without purification is employed for recrystallization of more crude nicotinamide.

14. A process according to claim 2 wherein all of the mother liquor without purification is employed for recrystallization of more crude nicotinamide.

15. A process according to claim 3 wherein all of the mother liquor without purification is employed for recrystallization of more crude nicotinamide.

16. A process according to claim 4 wherein all of the mother liquor without purification is employed for recrystallization of more crude nicotinamide.

* * * * *